US00PP08826P

United States Patent [19]

Hatten

[11] Patent Number: Plant 8,826

[45] Date of Patent: Jul. 12, 1994

[54] BOUGAINVILLEA HYBRID CV. SUNDANCE

[75] Inventor: William A. Hatten, Mobile, Ala.

[73] Assignee: Hatten's Nursery, Inc., Mobile, Ala.

[21] Appl. No.: 57,279

[22] Filed: Apr. 30, 1993

[51] Int. Cl.[5] ..... A01H 5/00

[52] U.S. Cl. ..... Plt./67.7

[58] Field of Search ..... Plt. 67.7

*Primary Examiner*—James R. Feyrer

*Attorney, Agent, or Firm*—Tilton Fallon Lungmus

[57] ABSTRACT

A new and distinct Bougainvillea particularly distinguished from other Bougainvillea plants by its yellow green non-woody stems, peduncles, and pedicels; its light yellow, light green and dark green variegated young leaves, and flower bracts which change from orange to empire rose as they mature.

1 Drawing Sheet

BACKGROUND OF THE NEW PLANT

This invention relates to a new and distinct selection of Bougainvillea, a member of the Nyctaginaceae family, which was discovered in 1988 by me as a spontaneous bud sport occurring in a potted specimen of a group of the Bougainvillea hybrid cultivar Alabama Sunset (unpatented) being grown in a commerical greenhouses in Mobile, Ala. In the Summer of 1988, a number of cuttings were propagated from this sport. The following summer, one plant in the group was observed to be distinctly different and superior to the others. Because of the high quality growth habit, and the pleasing coloration of this plant, it was selected by me for propagation. Asexual reproduction of this plant by cuttings at my nursery in Mobile, Ala., has continued from generation to generation and shows that its characteristics remain fixed, and that its homogeneity can be assured.

BRIEF DESCRIPTION OF THE DRAWING

The accompanying photographic drawing shows a typical specimen of the plant, in full bloom, the color rendition being as nearly true to that herein specified as is reasonably possible to obtain by professional photographic procedures.

DESCRIPTION OF THE NEW PLANT

The following is a detailed description of my new Bougainvillea variety based upon observation of plants grown in greenhouse as well as outdoors at Mobile, Ala., and blooming during the current year. The color designations stated herein are according to R.H.S. Colour Chart published by the Royal Horticultural Society of London. The illustration clearly shows the orange and pink colors of the bracts, the light and dark green variegation of the new foliage, and the yellowish color of the stems and peduncles.

THE PLANT

Origin: Spontaneous Sport.

Parentage: Alabama Sunset (unpatented) originated 1980, parentage unknown). cv. Alabama Sunset is a well-known commercial variety.

Classification: Bougainvillea.

Form: Family Nyctaginaceae. Medium vining shrub well suited for pot, hanging basket and tub culture. Also suitable for landscape plantings in frost free areas. This shrub is cascading with long, leafy, wand-like branches.

Growth habit: Mounding one cascading with long, leafy, wand like branches. Leaf node spacing is one to five cm. When grown in a container, the overall growth of the main branches should be less than one meter per year. After one year of growth, the diameter of the lateral branches varies from 6 to 10 mm at their base, tapering to 2 mm at the terminal bud. The shape is mounding and cascading. Pruning is necessary once to twice per year. The plant is very tolerant of pruning and its shape and appearance is enhanced by several prunings per year. Two to four lateral branches will be produced on each stem that is pruned. The density of the canopy and number of flowers is vastly improved with pruning.

Training or staking is not required when grown in hanging baskets or pots up to five gallon capacity. However, the plant is readily adaptable to training on a trellis or training as a tree-form specimen if staked. Soft pruning or pinching can be utilized to produce more lateral branches and foliage. This method will produce a full and compact plant that can be maintained in a container for a number of years. As flowering occurs on new growth, pinching and pruning results in more lateral branches, a greater display of color and slower lateral growth. Outdoor plantings in frost-free areas should also be treated as above. If left unpruned, the limbs would grow between one and two meters per year depending on prevailing conditions.

Flowering: Profuse and free flowering in Southern Alabama from December to October.

Bark: Mature bark is smooth to slightly rough and woody ranging in color from 177-C to 177-B.

THE FLOWER

Corolla: Absent.

Calyx: Salverform, tube: 1.6 cm long (±0.2 cm). All pubescence of the calyx consists of short, ascending curved hairs.

*Outer surface.*—Sparsely puberulent, tube greenish-orange with a 5 prominent longitudinal ribs constructed above the mid-point of the tube.

*Inner surface.*—Green, glabrous and lustrous, 5 lobes, revolute, upper surface of the lobes whitish pink and puberulent-tomentose along the edges, lower surface of the lobes pink-orange with green vein, puberulent-tomentose.

*Calyx petaloids.*—Number: Ten. Arrangement: Attached in fused pairs between the calyx lobes. Color: White to whitish pink. Margins: Slightly erose.

Arrangement: Flowers in clusters of three, the pedicil of each adnate to the midrib of a showy bract up to the base of the calyx tube, the three bracts closely appressed at their bases and attached at the top of the ultimate branches of the peduncles.

Flower bract: Averages 4 sets of bracts per peduncle, while cv. Alabama Sunset averages 3.

*Color.*—Changing from orange 30-C to empire rose 48-D with age coloring that is identical to cv. Alabama Sunset.

*Size.*—Length: 3.3–3.7 cm long. Width: 3.0–3.5 cm wide.

*Shape.*—Ovate to broadly elliptic.

*Margins.*—Undulate, glabrous.

*Apex.*—Acute.

*Base of bract.*—Cordate.

Foliage:

*Arrangement.*—Alternate.

*Size.*—Foliage size varies depending on age — Length 5.0–7.6 cm. Width: 5.0–6.2 cm wide.

*Color.*—New growth —144-B along the midrib and green 137-A along the outer portions. Older growth — uniformly green 137-A. This differs from cv. Alabama Sunset, which is uniformly green 137-A.

*Shape.*—Ovate to broadly elliptic, base broadly acute to rounded.

*Margins.*—Entire, occasionally slightly undulate.

*Pubescence.*—Minutely puberulent, with short ascending curved hairs, on upper and lower surfaces on midrib and larger veins and on petioles.

Stems:

*Color.*—Varying from yellow-green 153-D to red 37-A, differing from cv. Alabama Sunset which is green 137-C. This is also true of its pedicles or peduncles coloration.

*Pubescence.*—Sparsely puberulent (with short ascending, curved hairs) denser at short apexes.

*Spines.*—Yellowish, slightly recurved, sparse.

*Length.*—0.5–0.6 cm.

REPRODUCTIVE ORGANS

Stamens:

*Number.*—8.

*Arrangement.*—The stamens are included in the calyx tube on unequal filaments, one or two reaching the apex of the calyx tube, fused only at their extreme basis.

Pistils:

*Number.*—1.

*Form.*—Containing 1 ovule, ovary stipitate, style lateral, shorter than the surrounding stamen filaments.

Fertility: Pollen and ovary sterile, probably due to interspecific hybridization in its remote background.

As is typical of Bougainvilleas, the intensity of the bright color is dependent upon the climate, quality and the intensity of the sunlight in the growing area. All observations stated herein are based on Bougainvillea hybrid CV. Sundance growing and blooming in mid summer in Mobile, Ala., in a greenhouse covered with one layer of 6 mil uv resistant polyethylene sheeting. Bougainvillea hybrid CV. Sundance differs from its parent, Bougainvillea hybrid CV. Alabama Sunset in its yellow-green tone of its young foliage, its more floriferous and longer blooming season than its parent, and the unusual coloration of its foliage, stems, peduncles and pedicels.

I claim:

1. A new and distinct variety of Bougainvillea plant as substantially shown and described herein, characterized by its unique combination of floriferous habit, orange colored bracts, which change to empire rose-color as they mature, light and dark green leaf variegation of new growth, and its yellowish stems, peduncles and pedicels.

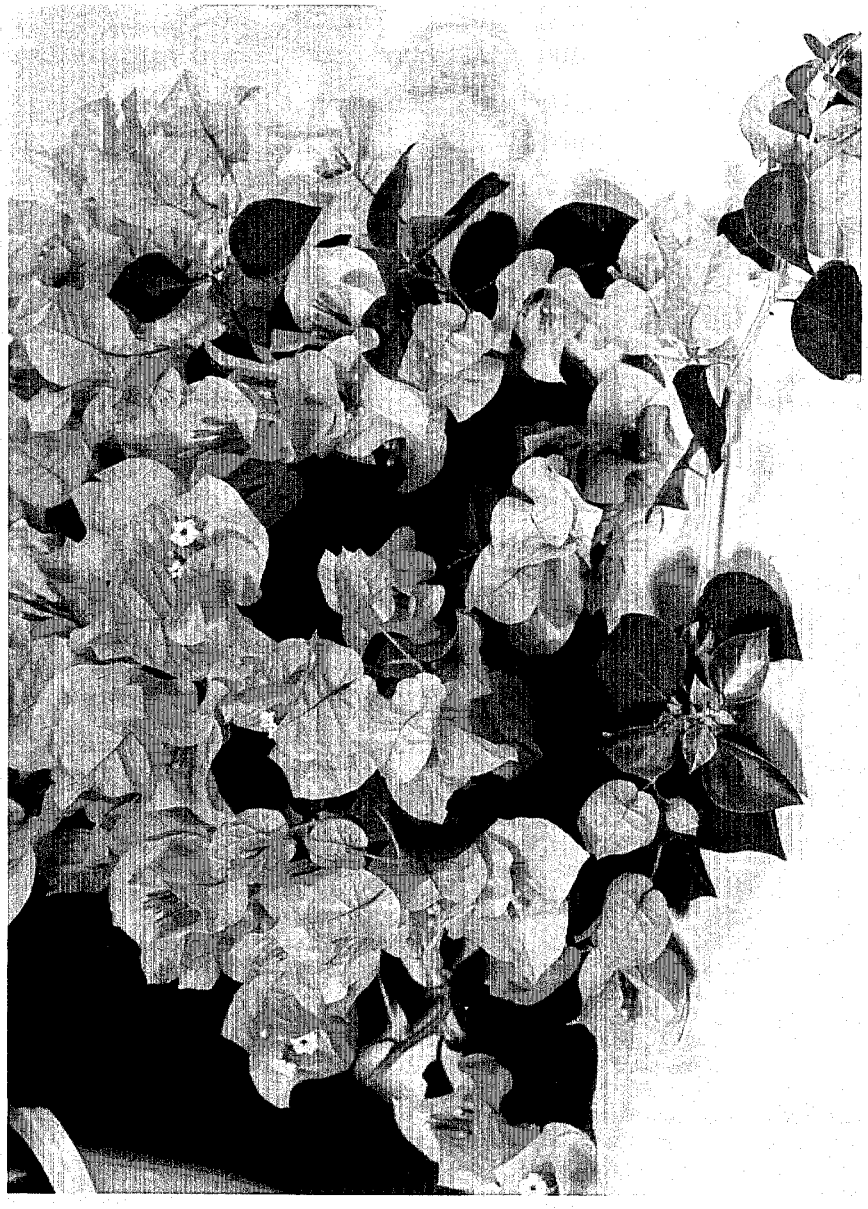

* * * * *